(12) United States Patent
Crawley et al.

(10) Patent No.: US 9,987,267 B2
(45) Date of Patent: Jun. 5, 2018

(54) TRANSDERMAL FORMULATIONS OF PERGOLIDE AND USES THEREOF

(71) Applicant: Elanco US Inc., Indianapolis, IN (US)

(72) Inventors: Sara Elizabeth Crawley, Noblesville, IN (US); Amy Louise Marr, Greenfield, IN (US); Jane Granville Owens, Indianapolis, IN (US)

(73) Assignee: Elanco US Inc., Greenfield, IN (US)

( * ) Notice: Subject to any disclaimer, the term of this patent is extended or adjusted under 35 U.S.C. 154(b) by 0 days. days.

(21) Appl. No.: 15/314,727

(22) PCT Filed: Jun. 11, 2015

(86) PCT No.: PCT/US2015/035237
§ 371 (c)(1),
(2) Date: Nov. 29, 2016

(87) PCT Pub. No.: WO2015/195448
PCT Pub. Date: Dec. 23, 2015

(65) Prior Publication Data
US 2017/0095468 A1 Apr. 6, 2017

Related U.S. Application Data

(60) Provisional application No. 62/013,819, filed on Jun. 18, 2014.

(51) Int. Cl.
| | |
|---|---|
| *A61K 31/135* | (2006.01) |
| *A61K 31/44* | (2006.01) |
| *A61K 31/24* | (2006.01) |
| *A61K 31/48* | (2006.01) |
| *A61K 47/20* | (2006.01) |
| *A61K 47/10* | (2017.01) |
| *A61K 47/22* | (2006.01) |
| *A61K 9/00* | (2006.01) |
| *A61K 9/08* | (2006.01) |

(52) U.S. Cl.
CPC ............ *A61K 31/48* (2013.01); *A61K 9/0017* (2013.01); *A61K 9/08* (2013.01); *A61K 47/10* (2013.01); *A61K 47/20* (2013.01); *A61K 47/22* (2013.01)

(58) Field of Classification Search
CPC .................................................... C07D 471/04
USPC ........................................................ 514/285
See application file for complete search history.

(56) References Cited

U.S. PATENT DOCUMENTS

| | | |
|---|---|---|
| 5,376,645 A | 12/1994 | Stella et al. |
| 2004/0120995 A1 * | 6/2004 | Martin ................... A61K 31/48 424/449 |
| 2007/0015763 A1 | 1/2007 | Romano |
| 2007/0225379 A1 | 9/2007 | Carrara |
| 2008/0260825 A1 * | 10/2008 | Quik .................... A61K 31/198 424/472 |

FOREIGN PATENT DOCUMENTS

DE    198 21 788 C1    12/1999

OTHER PUBLICATIONS

Innera, M., et al., "Comparison of hair follicle histology between horses with pituitary pars intermedia dysfunction and excessive hair growth and normal aged horses," Veterinary Dermatology, vol. 24, pp. 212-e47 (2013).

* cited by examiner

*Primary Examiner* — Raymond J Henley, III
(74) *Attorney, Agent, or Firm* — Joseph Matthew Pletcher

(57) ABSTRACT

This invention provides transdermal non-patch pergolide formulations useful for the treatment of disease in an equine. The invention also provides methods for treating a disease in an equine by administering a formulation of the invention to an equine.

12 Claims, 2 Drawing Sheets

TRANSDERMAL FORMULATIONS OF PERGOLIDE AND USES THEREOF

Figure 1:
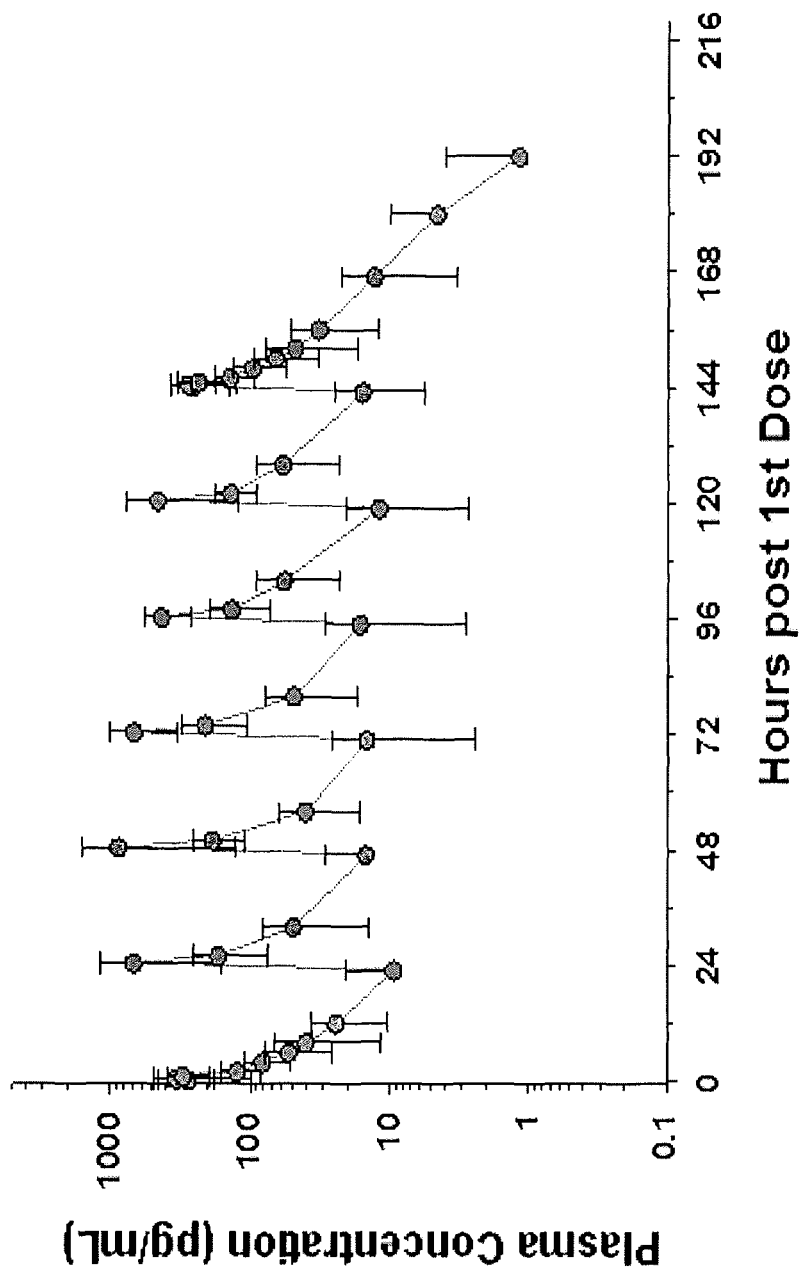

Equine Cushing's Disease (ECD), also known as Pituitary Pars Intermedia Dysfunction or PPID, is one of the most common hormonal disorders that occurs in equines. Hypertrophy and hyperplasia of the pituitary pars intermedia are often observed in ECD. The resulting clinical signs in equines may include hirsutism, polydipsia, polyuria, hyperhydrosis, protein catabolism (decreased muscle mass), episodes of laminitis, glucose intolerance and insulin refractoriness, suppression of the immune system, and general lethargy. ECD is a progressive disease mainly affecting aged equines (>15 years), but has been recognized in individuals as young as 7 years. The etiology and pathogenesis of ECD are not completely understood but are thought to derive from degeneration of the periventricular hypophyseal dopaminergic neurons and concomitant loss of dopaminergic inhibition of POMC-derived peptides. Prognosis tends to be associated with the prevalence of laminitis in the equine as the effects of this clinical sign are usually most severe.

Pergolide is an ergoline derivative which exhibits potent dopaminergic agonist activity at both $D_1$ and $D_2$ dopamine receptors and also decreases plasma prolactin concentrations. The compound is useful in treating physiological manifestations associated with hyperprolactinemia. Pergolide is considered to be a standard of care for the treatment of ECD and is typically administered orally to equines. An oral tablet for daily administration is available in some countries. However, the tablet can be difficult to administer orally due to the tablet's poor palatability in equines, the large size of equines, and the efforts required to force swallowing by the equines, which are compounded by the need to dose the oral tablet daily. Various oral suspensions and powders of pergolide can be compounded by a pharmacist for veterinary use. However, limitations of compounded pergolide formulated for oral dosing include the variation in dosages due to fluctuations in compounding techniques, the poor stability of the formulations, the lack of consistent potency of the formulations, and the potential difficulty in administering the compounded formulations to equines.

Various methods to deliver pergolide to equines have been attempted in order to overcome limitations of oral administration. For example, methods of transdermal application such as patches have potential advantages over oral administration, including non-invasive dosing, avoidance of the gastrointestinal tract, lack of first pass metabolism, steady, continuous drug delivery rather than a peak and trough phenomenon, potential reduction of side effects by elimination of peaks, possible reduction of lack of effectiveness due to elimination of troughs, and reduced dose frequency for convenience and increased compliance. Transdermal delivery of pergolide in a patch formulation has been evaluated in various animals, including humans and rats. However, the use of a transdermal patch to deliver pergolide to equines introduces additional shortcomings, including the potential absence or non-reproducibility of systemic pergolide exposure in equines, the possibility of damage to patches applied to equines, and the possibility of consumption of patches applied to equines and subsequent toxicity to the equines following consumption.

Investigation into non-patch transdermal formulations for equines has also encountered problems. Attempts at employing transdermal solutions as described generally in the art have resulted in plasma levels of pergolide which are below expected therapeutic values. One issue with the art's non-patch transdermal formulations is that the amount of pergolide, or a salt thereof, which is able to be solublized is, somewhat surprisingly, lower than what is needed to obtain therapeutic plasma concentrations.

Therefore, there exists a need for pergolide formulations which overcome some or all of the limitations of orally, patch, or other transdermal (non-patch) delivered pergolide in order to benefit treatment of equines in veterinary medicine. Accordingly, the present invention provides formulations of pergolide, or a salt thereof, which exhibits desirable properties and provides related advantages for treatment of diseases in equines.

The present invention demonstrates that the dermal barrier to drug permeation can be overcome in equines by using certain transdermal (non-patch) formulations having a sufficient amount of pergolide, or a salt thereof, solubilized therein. Through what is believed to be deposition of pergolide in the stratum corneum of an equine followed by prolonged systemic absorption, the present invention overcomes the limitations of pergolide administered in an oral formulation, a transdermal patch formulation, or other transdermal (non-patch) formulations.

The invention also provides methods for the treatment of disease in an equine comprising transdermally administering a formulation of the invention to the equine. As used herein, the term "equine" refers to any member of the horse family, including for example horses, ponies, miniature horses, miniature ponies, donkeys, mules, and zebras. The methods according to the present invention utilize a transdermal administration. As used herein, the term "transdermal" has its ordinary meaning in the art and refers to passage of an agent across at least one skin layer of an equine. As used herein, the term "disease" refers to any disorder, pathology, or condition in equines capable of being treated with pergolide or a salt thereof. In one embodiment, the disease is Equine Cushing's Disease, also known as Pituitary Pars Intermedia Dysfunction (PPID).

The present invention provides several advantages. First, the formulations of the invention can be administered to equines at a lower dosing frequency compared to orally-administered pergolide. For example, the dosing can be every other day, or once every three, four, five, six, or seven days. Second, the present invention has an advantageous ease of administration in equines compared to administration of oral formulations of pergolide. Third, the present invention can be formulated in a more uniform solution that is not subject to the widely fluctuating concentrations and formulations of pergolide oral solutions that result from non-uniform solution compounding by a variety of pharmacists.

Fourth, use of the present invention provides advantages compared to pergolide administered to equines in a patch formulation. For example, the present invention provides for pergolide administration in a formulation that is not easily damaged or consumed by equines compared to pergolide administered to equines in a patch formulation. Moreover, because the present invention is a transdermal non-patch formulation and not a device, the invention does not require the maintenance of skin contact in equines to maintain appropriate pergolide absorption. The formulations of the invention also provide for a therapeutic concentration of pergolide in the equine's plasma.

The formulations of the present invention comprise pergolide or a salt thereof. Pergolide is also known by chemical names such as D-6-n-propyl-8β-methylmercaptomethylergoline, or (8β)-8-[(Methylthio)methyl]-6-propylergoline. The chemical structure of pergolide is:

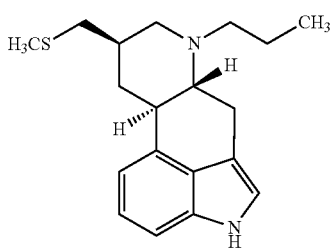

As used herein, the pergolide includes pergolide and the pharmaceutically acceptable salts of pergolide. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when pergolide and any of its intermediates containing a basic functionality are reacted with a pharmaceutically acceptable acid. Pharmaceutically acceptable acids commonly employed to form such acid addition salts include inorganic and organic acids. In one embodiment, a pharmaceutically acceptable salt of pergolide is the mesylate salt.

The formulations employ a solvent system which includes one or more solvents. For the formulations of the invention, the solvents employed in the solvent system include at least one of dimethyl sulfoxide, N-methylpyrrolidone, dimethylformamide, tetrahydrofuran, benzyl alcohol, acidic water, polypropylene glycol, methanol, a polyoxyethylene sorbitan monoester, water with about 40% of a cyclodextrin, dimethyl isosorbide, a caprylic/capric acid glyceride, or a suitable $C_8$-$C_{10}$ polyglycolized glyceride, and includes suitable mixtures of the above. The solvent system provides the desired solubility of pergolide or a salt thereof, which is 5 mg/ml and higher, and about 25 mg/ml and higher, in the solvent system.

Acidic water is water having a pH of less than 7, which includes a pH of less than 6, less than 5, less than 4, less than 3, and less than 2, as well as having a pH in the range of 1-2, 1-3, 1-4, 1-5, 1-6, 2-3, 2-4, 2-5, 2-6, 3-4, 3-5, 3-6, 4-5, 4-6, and 5-6.

Polyoxyethylene sorbitan monoesters include, for example, polysorbate 80 (polyoxyethylenesorbitol monooleate, Tween® 80, BASF Aktiengesellschaft) and Solutol® HS-15 (polyoxyethyleneglycol 660 hydroxystearate, BASF Aktiengesellschaft, CAS Number 70142-34-6).

Cyclodextrins include those described in U.S. Pat. Nos. 6,046,177; 5,874,418, 5,376,645, and 5,134,127. Particular cyclodextrins include those marketed under the Kleptose® (such as HPD and HP), and Captisol® (CAS Number 182410-00-0) brands.

Caprylic/capric acid glycerides are those esterification products of caprylic and/or capric acid with glycerol, and are exemplified by those comprising or consisting mainly or essentially of caprylic/capric acid mono- and di-glycerides such as are commercially available under the trade name Imwitor®. A particular caprylic/capric acid glyceride product of this class is Imwitor® 742, which is the esterification product of a mixture of ca. 60 p.p.w. caprylic acid and ca. 40 p.p.w. capric acid with glycerol.

A suitable polyglycolized glyceride is a $C_8$-$C_{10}$ polyglycolized glyceride having a Hydrophilic-Lipophilic-Balance (HLB) of 5 to 16, and in another embodiment having an HLB of about 10 to about 16. Suitable polyglycolized glycerides are exemplified by those marketed under the brand Labrasol®.

2-(2-Ethoxyethoxy)ethanol is available as Transcutol®.

The formulations may employ a volatile liquid in the solvent system. As used herein, the term "volatile liquid" refers to an additional solvent in the solvent system which is more volatile (more readily vaporizable at low temperatures or tends to evaporate more rapidly) than the other solvent(s) in the solvent system. For example, a volatile liquid may be readily vaporizable at low temperatures or tends to evaporate rapidly. The volatile liquid will act as a solubilizer for the pergolide or salt thereof, particularly before administration. The volatile liquid may also act as a penetration enhancer, helping to transition the pergolide or salt thereof and/or the other solvent(s) into the stratum corneum. The volatile liquid will evaporate relatively quickly, leaving a dry-feeling and avoiding dripping. Further, rapid evaporation of the volatile liquid can result in super-saturation of other ingredients of the formulation, avoiding crystallization of the ingredients and increasing the bioavailability of the pergolide or salt thereof. In some embodiments, volatile liquids according to the present invention include safe skin-tolerant solvents. In some embodiments, the volatile liquid is a lower alkyl alcohol or a mixture of such alcohols. In some embodiments, the volatile liquid is selected from the group consisting of ethanol, ethyl acetate, isopropanol, acetone, ethyl formate, methanol, methyl acetate, methyl ethyl ketone, pentanol, chloroform, and benzyl alcohol, or a mixture thereof. In other embodiments, the volatile liquid is benzyl alcohol.

The therapeutic amount of the formulations of the invention may vary from one equine to another and can depend upon a number of factors, including the overall physical condition of the equine and the underlying cause of the condition to be treated. In some embodiments, the amount of pergolide, or salt therein, present in the formulation is about 0.05 to about 0.5 milligram per kilogram of equine body weight. In another embodiment, the therapeutically effective amount of pergolide, or salt thereof, present in the formulation is about 0.05 to about 0.3 milligrams per kilogram of equine body weight.

In some embodiments, the single dose transdermal formulation of the formulation comprises between about 0.5 and about 10 mL of a solution of the formulation. In some embodiments, the single dose transdermal formulation of the formulation comprises between about 1 and about 8 mL of a solution of the formulation. In some embodiments, the single dose transdermal formulation of the formulation comprises between about 1 and about 5 mL of a solution of the formulation. In some embodiments, the single dose transdermal formulation of the formulation comprises between about 1 and about 3 mL of a solution of the formulation. In one embodiment, the formulations according to the present invention have a total volume of about 3 ml.

In one embodiment, the formulations according to the present invention have about 10 to about 150 mg of pergolide, or a salt thereof, therein. In one embodiment, the formulations according to the present invention have about 25 to about 150 mg of pergolide, or a salt thereof, therein. In one embodiment, the formulations according to the present invention have about 25 to about 120 mg of pergolide, or a salt thereof, therein. In one embodiment, the formulations according to the present invention have about 30 to about 120 mg of pergolide, or a salt thereof, therein. In one embodiment, the formulations according to the present invention have about 30 to about 100 mg of pergolide, or a salt thereof, therein. In one embodiment, the formulations according to the present invention have about 30 to about 95 mg of pergolide, or a salt thereof, therein. In one embodiment, the formulations according to the present invention have about 35 to about 95 mg of pergolide, or a salt thereof, therein. In one embodiment, the formulations according to the present invention have about 35 to about 80 mg of pergolide, or a salt thereof, therein. In one embodiment, the formulations according to the present invention have about 60 to about 80 mg of pergolide, or a salt thereof, therein.

In some embodiments of the present invention, the formulation is administered for the treatment of Equine Cushing's Disease. In one embodiment, the formulation is administered for the treatment of Equine Cushing's Disease as an acute therapy. In another embodiment, the formulation is administered for the treatment of Equine Cushing's Disease as a chronic therapy. As used herein, "chronic" generally refers to regular administration for an extended period of time. For example, chronic administration encompasses administration that provides sufficient therapeutic blood plasma concentrations on a regular basis. For example, such administration may include administration every other day, once every three, four, five, six, or seven days, for one, two, three, four, five, six, seven, eight, nine, ten, eleven, or twelve months, or for over a year.

In one embodiment of the present invention, the formulation is contained in a multiple-dose vial prior to administration. The multiple-dose vial containing the formulation of the present invention can be made of glass, plastic, or other material. In one embodiment of the present invention, the formulation is administered as a multiple dose regimen. In one embodiment of the present invention, the formulation is administered as a single dose. In yet another embodiment of the present invention, the formulation is administered as a single unit dose. As used herein, the term "unit dose" is a discrete amount of the formulation comprising a predetermined amount of pergolide or a salt thereof.

In one embodiment, the formulation can be transdermally administered to the equine at a location from which the hair is clipped. In another embodiment, the formulation can be transdermally administered to the equine at a location from which the hair is not clipped. In one embodiment, the formulation can be transdermally administered to the equine at a location at which the skin is cleaned. For example, the skin of the equine can be cleaned with a disinfectant solution. In another embodiment, the formulation can be transdermally administered to the equine at a location at which the skin is not cleaned.

In one embodiment of the present invention, the formulation is transdermally administered to an equine at a dorsal or dorsum location of the equine. According to the methods of the present invention, the term "dorsal" has its ordinary meaning and as used herein refers to the location on the top of the animal, i.e., along the equine's back. In one embodiment, the formulation can be administered to the clipped or non-clipped dock (tail root) of the horse. In one embodiment of the present invention, the formulation is transdermally administered to an equine at a ventral location of the equine. According to the methods of the present invention, the term "ventral" has its ordinary meaning and as used herein refers to the direction towards the abdomen of an equine, i.e., along the underside of the equine's body.

In another embodiment of the present invention, the formulation is transdermally administered to an equine at a location on the foreleg of the equine. According to the methods of the present invention, the term "foreleg" has its ordinary meaning and as used herein refers to any proximal or distal location on either of an equine's forelegs. In yet another embodiment of the present invention, the formulation is transdermally administered to an equine at a location on the hind leg of the equine. According to the methods of the present invention, the term "hind leg" has its ordinary meaning and as used herein refers to any proximal or distal location on either of an equine's hind legs.

In one embodiment of the present invention, the formulation is transdermally administered to an equine at a location on the neck of the equine. According to the methods of the present invention, the term "neck" has its ordinary meaning and as used herein refers to any location on either side of the neck. In another embodiment of the present invention, the formulation is transdermally administered to an equine at a location near the mane.

In yet another embodiment of the present invention, the formulation is transdermally administered to an equine at a location underneath the mane. This embodiment may offer further advantages of the present invention because of the mane may protect the administrator (e.g., an owner or caretaker) from the site of administration. Thus, accidental absorption of the formulation by the administrator may be minimized.

In one embodiment of the present invention, the formulation is transdermally administered to an equine at a dorsal location wherein the dorsal location is the upper, mid-cervical region under the mane of the equine. The formulation can be administered to the equine in a single line, or in multiple lines, on the dorsal location. In one embodiment, the single line on the dorsal location is approximately four inches long. In another embodiment, the administration may be in a spot. In another embodiment, the administration may be in a line.

The formulations and methods of the present invention include those that also optionally contain one or more other active ingredients, in addition to pergolide or a salt thereof. As used herein, the term "active ingredient" or "therapeutic ingredient" refers to a therapeutically active compound, as well as any prodrugs thereof and pharmaceutically acceptable salts, hydrates, and solvates of the compound and the prodrugs. Other active ingredients may be combined with pergolide and may be either administered separately or in the same pharmaceutical formulation. The amount of other active ingredients to be given may be readily determined by one skilled in the art based upon therapy with pergolide.

In some embodiments, the single dose transdermal formulation effectively treats a disease in the equine for an effective period of time. In some embodiments, an effective period of time comprises a period of at least 48 hours, a period of at least 72 hours, a period of at least 96 hours (i.e., 4 days), a period of at least 5 days, a period of at least 7 days, a period of at least 10 days, a period of at least 14 days, a period of at least 21 days, a period of at least 28 days, or a period of at least 30 days. In one embodiment, the single dose transdermal formulation is administered once every at least 48 hours. In another embodiment, the single dose transdermal formulation is administered once every at least 72 hours. In yet another embodiment, the single dose transdermal formulation is administered once every at least 96 hours. In another embodiment, the single dose transdermal formulation is administered once every at least 5 days. In another embodiment, the single dose transdermal formulation is administered once every at least 7 days.

In one embodiment, provided is a formulation comprising pergolide or a salt thereof, and a solvent system comprising one or more solvents selected from dimethyl sulfoxide, N-methylpyrrolidone, dimethylformamide, tetrahydrofuran, benzyl alcohol, acidic water, polypropylene glycol, methanol, a polyoxyethylene sorbitan monoester, water with about 40% of a cyclodextrin, dimethyl isosorbide, a caprylic/capric acid glyceride, or a suitable $C_8$-$C_{10}$ polyglycolized glyceride, wherein the solubility of said pergolide or salt thereof in said solvent system is 5 mg/ml or higher. In another embodiment, the pergolide or salt thereof is the pergolide free base and said one or more solvents are selected from dimethyl sulfoxide, N-methylpyrrolidone, dimethylformamide, tetrahydrofuran, benzyl alcohol, acidic water, Solutol® HS15, water with about 40% Kleptose®, dimethylisosorbide, Imwitor® 742, or Labrasol®. In another embodiment, the pergolide or salt thereof is the pergolide free base and said one or more solvents are selected from dimethyl sulfoxide, N-methylpyrrolidone, dimethylformamide, or tetrahydrofuran. In another embodiment, the pergolide or salt thereof is the pergolide mesylate and said one or more solvents are selected from dimethyl sulfoxide, N-methylpyrrolidone, dimethylformamide, tetrahydrofuran, benzyl alcohol, acidic water, polypropylene glycol, methanol, Solutol® HS15, or water with about 40% Captisol®. In another embodiment, the pergolide or salt thereof is the pergolide mesylate and said solvent is selected from dimethyl sulfoxide, N-methylpyrrolidone, dimethylformamide, tetrahydrofuran, benzyl alcohol, acidic water, or water with 40% Captisol®. In another embodiment, the solvent system further comprises at least one volatile liquid which is different than said solvent. In another embodiment, the formulation comprises pergolide mesylate, dimethyl sulfoxide, and polypropylene glycol. In another embodiment, the formulation comprises pergolide mesylate, dimethyl sulfoxide, benzyl alcohol, and polypropylene glycol. In another embodiment, the formulation comprises pergolide free base, dimethyl sulfoxide, benzyl alcohol, and 2-(2-ethoxyethoxy)ethanol. In another embodiment, the formulation comprises pergolide free base, dimethyl sulfoxide, benzyl alcohol, and dimethyl isosorbide.

In one embodiment, provided is a formulation comprising pergolide or salt thereof, and a solvent system comprising one or more solvents selected from dimethyl sulfoxide, N-methylpyrrolidone, dimethylformamide, tetrahydrofuran, benzyl alcohol, or water with about 40% Captisol®, wherein the solubility of said pergolide or salt thereof in said solvent system is about 25 mg/ml or higher. In one embodiment, the solvent system further comprises at least one volatile liquid which is different than said solvent. In one embodiment, the at least one volatile liquid is selected from the group consisting of ethanol, ethyl acetate, isopropanol, acetone, ethyl formate, methanol, methyl acetate, methyl ethyl ketone, pentanol, chloroform, and benzyl alcohol. In one embodiment, the pergolide or salt thereof is pergolide free base, and said one or more solvents are selected from dimethyl sulfoxide, N-methylpyrrolidone, dimethylformamide, or tetrahydrofuran. In one embodiment, the formulation comprises pergolide free base, dimethyl sulfoxide, benzyl alcohol, and 2-(2-ethoxyethoxy)ethanol. In one embodiment, the formulation comprises pergolide free base, dimethyl sulfoxide, benzyl alcohol, and dimethyl isosorbide. In one embodiment, the pergolide or salt thereof is pergolide mesylate, and said solvent is selected from dimethyl sulfoxide, N-methylpyrrolidone, dimethylformamide, tetrahydrofuran, benzyl alcohol, or water with about 40% Captisol®. In one embodiment, the formulation comprises pergolide mesylate, dimethyl sulfoxide, benzyl alcohol, and polypropylene glycol. In one embodiment, the formulation comprises pergolide mesylate, dimethyl sulfoxide, and polypropylene glycol. In one embodiment, the formulation comprises pergolide mesylate in about 40-50% dimethyl sulfoxide, about 20-25% benzyl alcohol, and about 25-35% polypropylene glycol. In one embodiment, the formulation comprises pergolide mesylate in about 40-50% dimethyl sulfoxide and about 50-60% polypropylene glycol. In one embodiment, the formulation comprises pergolide free base in about 40-50% dimethyl sulfoxide, about 20-30% benzyl alcohol, and about 20-30% 2-(2-ethoxyethoxy)ethanol. In one embodiment, the formulation comprises pergolide free base in about 40-50% dimethyl sulfoxide, about 30-40% benzyl alcohol, and about 10-20% dimethyl isosorbide. In one embodiment, the formulation comprises about 120 mg of pergolide mesylate in about 40-50% dimethyl sulfoxide, about 20-25% benzyl alcohol, and about 25-35% polypropylene glycol. In one embodiment, the formulation comprises about 120 mg pergolide mesylate in about 40-50% dimethyl sulfoxide and about 50-60% polypropylene glycol. In one embodiment, the formulation comprises about 30 mg pergolide free base in about 40-50% dimethyl sulfoxide, about 20-30% benzyl alcohol, and about 20-30% 2-(2-ethoxyethoxy)ethanol. In one embodiment, the formulation comprises about 30 mg pergolide free base in about 40-50% dimethyl sulfoxide, about 30-40% benzyl alcohol, and about 10-20% dimethyl isosorbide. In one embodiment, the formulation comprises about 120 mg of pergolide mesylate in about 46.7% dimethyl sulfoxide, about 22.6% benzyl alcohol, and about 30.7% polypropylene glycol. In one embodiment, the formulation comprises about 120 mg pergolide mesylate in about 46.7% dimethyl sulfoxide and about 53% polypropylene glycol. In one embodiment, the formulation comprises about 30 mg pergolide free base in about 46.7% dimethyl sulfoxide, about 27.7% benzyl alcohol, and about 25.6% 2-(2-ethoxyethoxy)ethanol. In one embodiment, the formulation comprises about 30 mg pergolide free base in about 47.6% dimethyl sulfoxide, about 35.9% benzyl alcohol, and about 15.4% dimethyl isosorbide.

In one embodiment, the formulation is in a single unit dosage transdermal form. In one embodiment, the formulation comprises about 10 to about 150 mg of the pergolide or salt thereof. In one embodiment, the formulation is characterized in that said pergolide or salt thereof is provided in an amount of about 0.05 to about 0.50 mg/kg of the weight of an equine. In one embodiment, the formulation is characterized in that said pergolide or salt thereof is provided in an amount of about 0.05 to about 0.30 mg/kg of the weight of an equine. In one embodiment, the formulation is adapted to be administered once every other day to an equine. In one embodiment, the formulation is adapted to be administered once every 3, 4, 5, 6, or 7 days to an equine. In one embodiment, the formulation is adapted to be administered once every 7 days to an equine. In one embodiment, the formulation volume is about 1 to about 5 ml. In one embodiment, the formulation volume is about 3 ml.

The following clauses illustrate embodiments of the invention.

1. A formulation comprising pergolide or a salt thereof, and a solvent system comprising one or more solvents selected from dimethyl sulfoxide, N-methylpyrrolidone, dimethylformamide, tetrahydrofuran, benzyl alcohol, acidic water, polypropylene glycol, methanol, a polyoxyethylene sorbitan monoester, water with about 40% of a cyclodextrin, dimethyl isosorbide, a caprylic/capric acid glyceride, or a suitable $C_8$-$C_{10}$ polyglycolized glyceride, wherein the solubility of said pergolide or salt thereof in said solvent system is 5 mg/ml or higher.

2. The formulation of clause 1, wherein said pergolide or salt thereof is the pergolide free base and said one or more solvents are selected from dimethyl sulfoxide, N-methylpyrrolidone, dimethylformamide, tetrahydrofuran, benzyl alcohol, acidic water, Solutol® HS15, water with about 40% Kleptose®, dimethylisosorbide, Imwitor® 742, or Labrasol®
3. The formulation of clause 1, wherein said pergolide or salt thereof is the pergolide free base and said solvent is selected from dimethyl sulfoxide, N-methylpyrrolidone, dimethylformamide, tetrahydrofuran, benzyl alcohol, acidic water, Solutol® HS15, water with about 40% Kleptose®, dimethylisosorbide, Imwitor® 742, or Labrasol®
4. The formulation of any of clauses 1-3, wherein said pergolide or salt thereof is the pergolide free base and said one or more solvents are selected from dimethyl sulfoxide, N-methylpyrrolidone, dimethylformamide, or tetrahydrofuran.
5. The formulation of clause 1, wherein said pergolide or salt thereof is the pergolide mesylate and said one or more solvents are selected from dimethyl sulfoxide, N-methylpyrrolidone, dimethylformamide, tetrahydrofuran, benzyl alcohol, acidic water, polypropylene glycol, methanol, Solutol® HS15, or water with about 40% Captisol®.
6. The formulation of clause 1, wherein said pergolide or salt thereof is the pergolide mesylate and said solvent is selected from dimethyl sulfoxide, N-methylpyrrolidone, dimethylformamide, tetrahydrofuran, benzyl alcohol, acidic water, polypropylene glycol, methanol, Solutol® HS15, or water with about 40% Captisol®.
7. The formulation of clause 1, 5 or 6, wherein said pergolide or salt thereof is the pergolide mesylate and said one or more solvents are selected from dimethyl sulfoxide, N-methylpyrrolidone, dimethylformamide, tetrahydrofuran, benzyl alcohol, acidic water, or water with 40% Captisol®.
8. The formulation of clause 1, 5, 6 or 7 comprising pergolide mesylate, dimethyl sulfoxide, and polypropylene glycol.
9. The formulation of any of clauses 1-8, wherein said solvent system further comprises at least one volatile liquid which is different than said solvent.
10. The formulation of claim 9, wherein said at least one volatile liquid is selected from the group consisting of ethanol, ethyl acetate, isopropanol, acetone, ethyl formate, methanol, methyl acetate, methyl ethyl ketone, pentanol, chloroform, and benzyl alcohol, and mixtures thereof.
11. The formulation of clause 10, comprising pergolide mesylate, dimethyl sulfoxide, benzyl alcohol, and polypropylene glycol.
12. The formulation of clause 10, comprising pergolide free base, dimethyl sulfoxide, benzyl alcohol, and 2-(2-ethoxyethoxy)ethanol.
13. The formulation of clause 10, comprising pergolide free base, dimethyl sulfoxide, benzyl alcohol, and dimethyl isosorbide.
14. A formulation comprising pergolide or salt thereof, and a solvent system comprising one or more solvents selected from dimethyl sulfoxide, N-methylpyrrolidone, dimethylformamide, tetrahydrofuran, benzyl alcohol, or water with about 40% Captisol®, wherein the solubility of said pergolide or salt thereof in said solvent system is about 25 mg/ml or higher.
15. The formulation of clause 14, wherein said solvent system further comprises at least one volatile liquid which is different than said solvent.
16. The formulation of clause 15, wherein said at least one volatile liquid is selected from the group consisting of ethanol, ethyl acetate, isopropanol, acetone, ethyl formate, methanol, methyl acetate, methyl ethyl ketone, pentanol, chloroform, and benzyl alcohol, and mixtures thereof.
17. The formulation of clause 14, wherein said pergolide or salt thereof is pergolide free base, and said one or more solvents are selected from dimethyl sulfoxide, N-methylpyrrolidone, dimethylformamide, or tetrahydrofuran.
18. The formulation of clause 14, wherein said pergolide or salt thereof is pergolide free base, and said solvent is selected from dimethyl sulfoxide, N-methylpyrrolidone, dimethylformamide, or tetrahydrofuran.
19. The formulation of clause 14 or 17, comprising pergolide free base and dimethyl sulfoxide and further comprising benzyl alcohol, and 2-(2-ethoxyethoxy)ethanol.
20. The formulation of clause 14 or 17, comprising pergolide free baseand dimethyl sulfoxide and further comprising benzyl alcohol, and dimethyl isosorbide.
21. The formulation of clause 14, wherein said pergolide or salt thereof is pergolide mesylate.
22. The formulation of clause 14 or 21, comprising pergolide mesylate, dimethyl sulfoxide and benzyl alcohol, and further comprising polypropylene glycol.
23. The formulation of clause 14 or 21, comprising pergolide mesylate and dimethyl sulfoxide, and further polypropylene glycol.
24. The formulation of clause 14, comprising pergolide mesylate in about 40-50% dimethyl sulfoxide and about 20-25% benzyl alcohol, and further comprising about 25-35% polypropylene glycol.
25. The formulation of clause 14, comprising pergolide mesylate in about 40-50% dimethyl sulfoxide and further comprising about 50-60% polypropylene glycol.
26. The formulation of clause 14, comprising pergolide free base in about 40-50% dimethyl sulfoxide and about 20-30% benzyl alcohol, and further comprising about 20-30% 2-(2-ethoxyethoxy)ethanol.
27. The formulation of clause 14, comprising pergolide free base in about 40-50% dimethyl sulfoxide and about 30-40% benzyl alcohol, and further comprising about 10-20% dimethyl isosorbide.
28. The formulation of clause 14, comprising about 120 mg of pergolide mesylate in about 40-50% dimethyl sulfoxide and about 20-25% benzyl alcohol, and further comprising about 25-35% polypropylene glycol.
29. The formulation of clause 14, comprising about 120 mg pergolide mesylate in about 40-50% dimethyl sulfoxide and further comprising about 50-60% polypropylene glycol.
30. The formulation of clause 14, comprising about 30 mg pergolide free base in about 40-50% dimethyl sulfoxide, and about 20-30% benzyl alcohol, and further comprising about 20-30% 2-(2-ethoxyethoxy)ethanol.
31. The formulation of clause 14, comprising about 30 mg pergolide free base in about 40-50% dimethyl sulfoxide, and about 30-40% benzyl alcohol, and further comprising about 10-20% dimethyl isosorbide.
32. The formulation of clause 14, comprising about 120 mg of pergolide mesylate in about 46.7% dimethyl sulfoxide, and about 22.6% benzyl alcohol, and further comprising about 30.7% polypropylene glycol.

33. The formulation of clause 14, comprising about 120 mg pergolide mesylate in about 46.7% dimethyl sulfoxide and further comprising about 53% polypropylene glycol.

34. The formulation of clause 14, comprising about 30 mg pergolide free base in about 46.7% dimethyl sulfoxide, and about 27.7% benzyl alcohol, and further comprising about 25.6% 2-(2-ethoxyethoxy)ethanol.

35. The formulation of clause 14, comprising about 30 mg pergolide free base in about 47.6% dimethyl sulfoxide, and about 35.9% benzyl alcohol, and about 15.4% dimethyl isosorbide.

36. The formulation of any of clauses 1-35, wherein said formulation is in a single unit dosage transdermal form.

37. The formulation of clause 36, comprising about 10 to about 150 mg of the pergolide or salt thereof.

38. The formulation of clause 36 or 37, wherein said formulation is characterized in that said pergolide or salt thereof is provided in an amount of about 0.05 to about 0.50 mg/kg of the weight of an equine.

39. The formulation of 38, wherein said formulation is characterized in that said pergolide or salt thereof is provided in an amount of about 0.05 to about 0.30 mg/kg of the weight of an equine.

40. The formulation of any of clauses 36-39, wherein said formulation is adapted to be administered once every other day to an equine.

41. The formulation of any of clauses 36-39, wherein said formulation is adapted to be administered once every 3, 4, 5, 6, or 7 days to an equine.

42. The formulation of any of clauses 36-39, wherein said formulation is adapted to be administered once every 7 days to an equine.

43. The formulation of any of clauses 36-39, wherein said formulation volume is about 1 to about 5 ml.

44. The formulation of clause 43, wherein said formulation volume is about 3 ml.

45. A method for treating a disease in an equine comprising transdermally administering to the equine in need thereof a formulation of any of clauses 1-44.

46. The method of clause 45, wherein the disease is Equine Cushing's Disease.

47. The method of clause 45 or 46, wherein the formulation is administered as an acute therapy.

48. The method of clause 45 or 46, wherein the formulation is administered as a chronic therapy.

49. The method of any of clauses 45-48, wherein the formulation is applied to a dorsal location of the equine.

50. The method of clause 49, wherein the dorsal location is a mid-cervical region under the mane of the equine.

51. The method of any of clauses 45-48, wherein the formulation is applied to a location on the neck of the equine.

52. The method of any of clauses 45-48, wherein the formulation is applied to a ventral location of the equine.

53. The method of any of clauses 45-48, wherein the formulation is applied to a location on the foreleg of the equine.

54. The method of any of clauses 45-48, wherein the formulation is applied to a location on the hindleg of the equine.

55. The method of any of clauses 45-48, wherein the formulation is applied to the dock (tail root) of the equine.

56. The method of any of clauses 45-55, wherein the pergolide or salt thereof is provided at a dose of about 25 to about 150 mg.

57. The method of any of clauses 45-56, wherein the pergolide or salt thereof is provided at a dose of about 0.05 to about 0.30 mg/kg of the equine.

58. The method of any one of clauses 45-57, wherein the formulation is administered with one or more other therapeutic ingredients.

59. A formulation of any of clauses 1-44 for use in therapy.

60. A formulation of any of clauses 1-44 for use in treating a disease in an equine.

61. The formulation for use according to clause 60, wherein the disease is Equine Cushing's Disease.

62. The formulation for use according to clause 60 or 61, wherein the formulation is administered as an acute therapy.

63. The formulation for use according to clause 60 or 61, wherein the formulation is administered as a chronic therapy.

64. The formulation for use according to any of clauses 60-63, wherein the formulation is applied to a dorsal location of the equine.

65. The formulation for use according to clause 64, wherein the dorsal location is a mid-cervical region under the mane of the equine.

66. The formulation for use according to any of clauses 60-63, wherein the formulation is applied to a location on the neck of the equine.

67. The formulation for use according to any of clauses 60-63, wherein the formulation is applied to a ventral location of the equine.

68. The formulation for use according to any of clauses 60-63, wherein the formulation is applied to a location on the foreleg of the equine.

69. The formulation for use according to any of clauses 60-63, wherein the formulation is applied to a location on the hindleg of the equine.

70. The formulation for use according to any of clauses 60-63, wherein the formulation is applied to the dock (tail root) of the equine.

71. The formulation for use according to any of clauses 60-70, wherein the pergolide or salt thereof is provided at a dose of about 25 to about 150 mg.

72. The formulation for use according to any of clauses 60-70, wherein the pergolide or salt thereof is provided at a dose of about 0.05 to about 0.30 mg/kg of the equine.

73. The formulation for use according to any one of clauses 60-72, wherein the formulation is administered with one or more other therapeutic ingredients.

74. The use of a formulation of any of clauses 1-44 for the manufacture of a medicament for the treatment of Equine Cushing's disease in a equine.

Study 1: Comparative Study of a Transdermal Pergolide Mesylate Formulation Administered to Equines A formulation is formulated to comprise about 1.25% (w/v) (12.5 mg/ml) of pergolide mesylate, about 5% (w/v) of octyl salicylate, and about 94% (w/v) of methanol.

The formulation is transdermally administered to four horses weighing between 391 and 452 kg at a dose of about 10 mg. The formulation is transdermally administered to the skin of the equine in the upper, mid-cervical region under the mane. Following administration to the equines, the plasma concentration of pergolide is assayed at intervals of approximately 1, 2, 4, 6, 8, 12, 24, 36, 48, 60, 72, 84, 96, 108, 120, 144 and 168 hours post-administration. The lower limit of quantification for the plasma concentration of pergolide in equines is about 50 pg/mL. Following administration, plasma concentrations of pergolide are detectable, but are not quantifiable in all horses.

Study 2: Study of Four Transdermal Pergolide Free Base Formulations Administered to Equines This study is conducted to characterize the pharmacokinetics of pergolide free base when transdermally applied in four different transdermal formulations to the clipped and cleaned forelegs of 12 mature horses weighing between 456.5 and 576.5 kg. The formulations/treatments are:

1) 6 ml containing 36 mg of pergolide free base in padimate 0 in ethanol 5:95, pH adjusted to 3 with phosphoric acid (comparative formulation);

2) 6 ml containing 36 mg of pergolide free base in 10% dimethyl sulfoxide in ethanol, pH adjusted to 3 with phosphoric acid;

3) 4 ml containing 60 mg of pergolide free base in N-methyl pyrrolidone; and 4) 2 ml containing 80 mg of pergolide free base in dimethyl sulfoxide/ammonium phosphate buffer 90:10.

On Day 0 the formulations are administered to three horses per treatment group. Doses are divided equally between the left and right upper lateral forelegs which have been clipped and clean approximately 10 minutes prior to administration. Blood samples are collected into a sodium heparin and a K$_2$EDTA tube one hour prior to administration, at 1, 2, 4, 6, 8, 12, 24, 48, 72, 96, and 120 hours post-administration. The lower limit of quantification for the plasma concentration of pergolide is about 5 pg/ml.

Pergolide is quantifiable in all horses through 120 hours post dose. Average $C_{max}$ ranges from 632 ng/ml for Treatment 3 to 2867 ng/ml for Treatment 4. Maximum concentrations are highly variable, with CV's greater than 40% for each treatment group. The average half-life ranges from 31.5 hours for Treatment 4 to 56.2 hours for Treatment 3. Despite a large difference in the amount of drug applied by the different treatments, AUC$_{(0-last)}$ remains relatively consistent, from 20,433 pg/ml*hr for Treatment 3 to 31,235 pg/ml*hr for Treatment 4.

Study 3: Study of Pergolide Mesylate Administered Orally, Subcutaneously, and Transdermally to Equines This study is conducted to characterize the pharmacokinetics of pergolide mesylate when administered orally, subcutaneously, or transdermally to five horses weighing between 510 to 551 kg. The three treatments are:

1) Subcutaneous injection (SC): 1 ml of a 2 mg/ml solution in 20% Captisol® in water (2 mg dose of pergolide mesylate);

2) Oral (PO): Prascend® tablet (1 mg dose of pergolide mesylate); and

3) Transdermal (TD): 4 ml of 15 mg/ml solution in N-methyl pyrrolidone (NMP) (2 ml per foreleg/60 mg dose of pergolide mesylate).

Treatment 1 is injected in the axillary area. Treatment 3 is divided equally between the left and right upper lateral forelegs which have been clipped prior to treatment and cleaned with alcohol approximately 10 minutes prior to treatment. Blood samples are collected prior to treatment and at 0.25, 0.5, 1, 2, 4, 6, 8, 12, 24, 36, 48, 60, 72, 84, 96 120, 144, and 168 (treatment 3 only) hours after dosing for determination of plasma pergolide and prolactin concentrations. The lower limit of quantification for the plasma concentration of pergolide is about 5 pg/ml.

Pergolide is quantifiable in all horses through 48 hours after treatment 1, through 12 hours after treatment 2, and through 144 hours after treatment 3. The average $C_{max}$ is quite consistent among the treatment groups ranging from 673 to 892 pg/ml. The average AUC$_{(0-last)}$ is markedly higher for the treatment 3 group compared to treatments 1 and 2 (12,149 vs 5,162 and 1,065 pg/ml*hr, respectively). Similarly, the average half-life of treatment 3 is longer than those observed for treatments 1 and 2 (29 vs 13 and 6 hours, respectively). The average $T_{max}$ is 1.1 hours for treatment 1, 0.35 hours for treatment 2, and 2.6 hours for treatment 3.

In comparison, in Study 2 pergolide free base is applied in the same formulation and similar dose as treatment 3 of Study 3. The $C_{max}$ observed in Study 2 is 632 pg/ml, similar to that for the present study's mesylate form in NMP. The average half-life is longer (56.2 hours) and the average AUC$_{(0-last)}$ is higher (20,433 pg/ml*hr) for the free base form in NMP compared to mesylate.

Study 4: Study of an Oral Pergolide Tablet Administered to Equines

In this comparative study, 1 mg pergolide mesylate tablets (Prascend® tablet) are given once a day orally for seven days to horses, for a total administration of 7 mg per horse. Blood samples are obtained one hour prior to dosing and at 15 min, 30 min, and 1, 2, 4, 6, 8, 12, and 23 hours after the initial dose. For days 2-6, blood samples are collected at 30 min, 2, 8, and 23 hours after each dose. For the final dose (dose 7), blood samples are obtained at 15 min, 30 min, 1, 2, 4, 6, 8, 12, 23, 36, 48, and 72 hours after the final dose. The lower limit of quantification for the plasma concentration of pergolide is about 5 pg/ml.

The oral administration produces an average AUC$_{0-168}$ of 10,702 pg/mL (±4108 Standard Deviation (SD)) over the course of treatment. Over all seven doses, $T_{max}$ ranges from 0.25 hr-1 hr, with the average value being 0.5 hrs post dose, and the half-life after the seventh dose ranges from 2.7 hrs to 13.29 hrs, with the average half-life being 8.35 hrs. The average $C_{max}$ for the first dose is 389.17 (±167.09) and for the seventh dose is 305.67 (±87.03), demonstrating little if any accumulation occurs over the dosing period. FIG. 1 sets out results of the study.

Study 5: Study of Pergolide Mesylate and Free Base Administered Transdermally to Equines This study is conducted to determine the pharmacokinetics of four different transdermal pergolide formulations when administered to the clipped dock (tail root) of 16 horses, weighing 425 to 562 kgs. The four treatment groups are:

1) 120 mg pergolide mesylate in 46.7% dimethyl sulfoxide/22.6% benzyl alcohol/30.7% polypropylene glycol (concentration of 30 mg/ml; equivalent to a dose of 92 mg of pergolide free base);

2) 120 mg pergolide mesylate in 46.7% dimethyl sulfoxide/53.0% polypropylene glycol (concentration of 30 mg/ml; equivalent to a dose of 92 mg of pergolide free base);

3) 30 mg pergolide free base in 46.7% dimethyl sulfoxide/ 27.7% benzyl alcohol/25.6% Transcutol® (concentration of 8 mg/ml); and 4) 30 mg pergolide free base in 47.6% dimethyl sulfoxide/ 35.9% benzyl alcohol/15.4% dimethyl isosorbide (concentration of 8 mg/ml).

Blood samples for determination of pergolide plasma concentrations are obtained within one hour prior to dosing and at 30 minutes, 1, 2, 4, 6, 8, 12, 24, 36, 48, 60, 72, 84, 96 120, 144, and 168 hours after dosing.

Pergolide is quantifiable in all horses through 168 hours following administration of treatments 1 and 3. Treatment 2 has quantifiable pergolide levels in all horses through 144 hours. Treatment 4 has quantifiable pergolide levels in all horses through 96 hours.

Treatment 1 has the following average (±SD) pharmacokinetic parameters: a half-life of 57.15 hours (±28.54), a $T_{max}$ of 4 hours (±1.63), a $C_{max}$ of 352.25 (±123.94), an $AUC_{(0-last)}$ of 10,746.80 hour*pg/ml (±5368.81), and an $AUC_{(0-inf)}$ of 11,773.7 of hour*pg/ml (±5876.04).

Treatment 2 has the following average (±SD) pharmacokinetic parameters: a half-life of 50.27 hours (±5.17), a $T_{max}$ of 5 hours (±2.58), a $C_{max}$ of 183.53 (±72.97), an $AUC_{(0-last)}$ of 6897.80 hour*pg/ml (±2754.93), and an $AUC_{(0-inf)}$ of 7647.02 hour*pg/ml (±3006.84).

Treatment 3 has the following average (±SD) pharmacokinetic parameters: a half-life of 75.40 hours (±30.52), a $T_{max}$ of 1.5 hours (±0.58), a $C_{max}$ of 231.00 (±111.36), an $AUC_{(0-last)}$ of 5189.74 hour*pg/ml (±1220.16), and an $AUC_{(0-inf)}$ of 6038.93 hour*pg/ml (±1423.58).

Treatment 4 has the following average (±SD) pharmacokinetic parameters: a half-life of 35.01 hours (±11.06), a $T_{max}$ of 2.5 hours (±1.73), a $C_{max}$ of 267.53 (±154.06), an $AUC_{(0-last)}$ of 4303.77 hour*pg/ml (±2120.35), and an $AUC_{(0-inf)}$ of 4599.74 hour*pg/ml (±2089.17).

Figure 2:
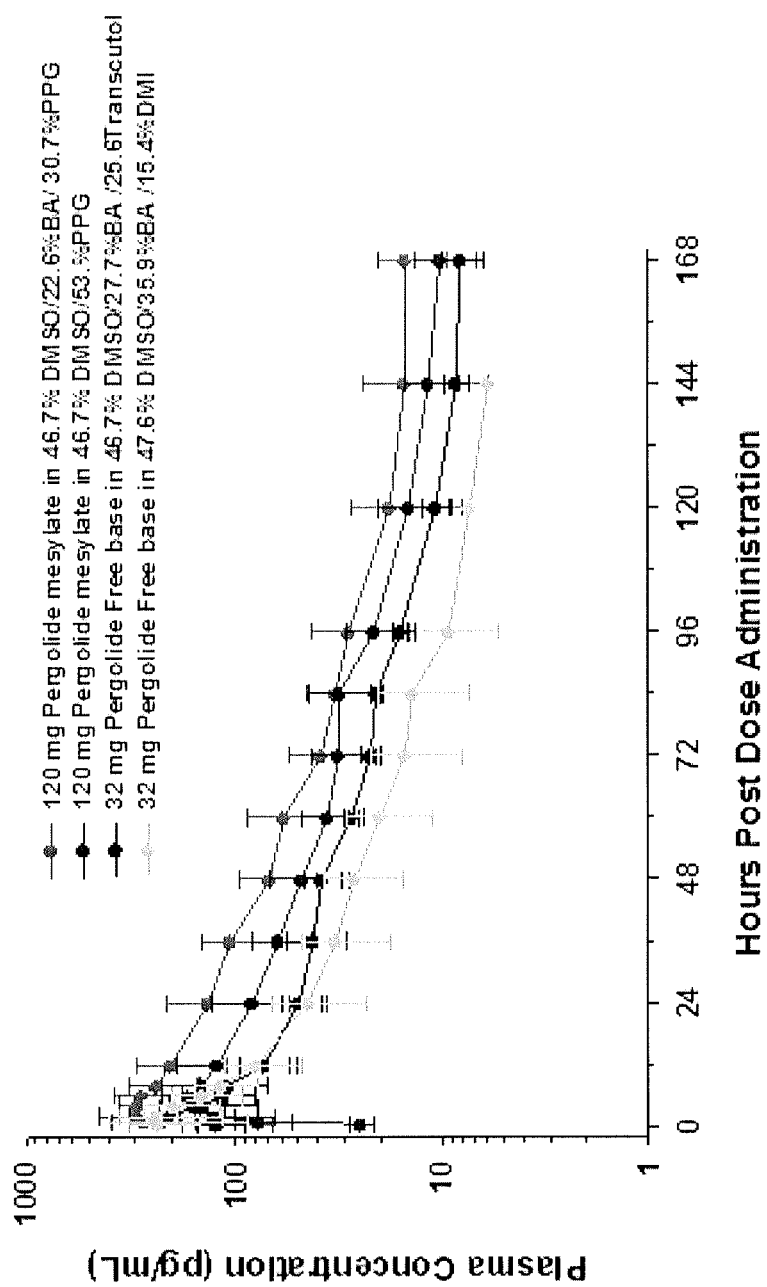

FIG. 2 sets out results of the study.

The invention claimed is:

1. A transdermal non-patch formulation comprising:
pergolide or a salt thereof; and
a solvent system comprising one or more solvents selected from dimethyl sulfoxide, N-methylpyrrolidone, dimethylformamide, tetrahydrofuran, benzyl alcohol, acidic water, polypropylene glycol, methanol, a polyoxyethylene sorbitan monoester, water with about 40% of a cyclodextrin, dimethyl isosorbide, a caprylic/capric acid glyceride, or a suitable $C_8$-$C_{10}$ polyglycolized glyceride;
wherein the solubility of said pergolide or salt thereof in said solvent system is 5 mg/ml or higher.

2. The formulation of claim 1, wherein said pergolide or salt thereof is the pergolide free base and said one or more solvents are selected from dimethyl sulfoxide, N-methylpyrrolidone, dimethylformamide, tetrahydrofuran, benzyl alcohol, acidic water, polyoxyethyleneglycol 660 hydroxystearate, water with about 40% of a cyclodextrin, dimethylisosorbide, the esterification product of a mixture of ca. 60 p.p.w. caprylic acid and ca. 40 p.p.w. capric acid with glycerol, or a suitable $C_8$-$C_{10}$ polyglycolized glyceride.

3. The formulation of claim 1, wherein said pergolide or salt thereof is the pergolide mesylate and said one or more solvents are selected from dimethyl sulfoxide, N-methylpyrrolidone, dimethylformamide, tetrahydrofuran, benzyl alcohol, acidic water, polypropylene glycol, methanol, polyoxyethyleneglycol 660 hydroxystearate, or water with about 40% of CAS Number 182410-00-0.

4. The formulation of claim 1, comprising pergolide or a salt thereof, and a solvent system comprising one or more solvents selected from dimethyl sulfoxide, N-methylpyrrolidone, dimethylformamide, tetrahydrofuran, benzyl alcohol, or water with about 40% of CAS Number 182410-00-0, wherein the solubility of said pergolide or salt thereof in said solvent system is about 25 mg/ml or higher.

5. The formulation of claim 4, wherein said solvent system further comprises at least one volatile liquid which is different than said solvent.

6. The formulation of claim 5, wherein said at least one volatile liquid is selected from the group consisting of ethanol, ethyl acetate, isopropanol, acetone, ethyl formate, methanol, methyl acetate, methyl ethyl ketone, pentanol, chloroform, and benzyl alcohol, and mixtures thereof.

7. The formulation of claim 4, wherein said pergolide or salt thereof is pergolide free base, and said one or more solvents are selected from dimethyl sulfoxide, N-methylpyrrolidone, dimethylformamide, or tetrahydrofuran.

8. The formulation of claim 4, comprising pergolide free base, dimethyl sulfoxide, and benzyl alcohol, and further comprising 2-(2-ethoxyethoxy)ethanol.

9. The formulation of claim 4, comprising pergolide free base, dimethyl sulfoxide, and benzyl alcohol, and further comprising dimethyl isosorbide.

10. The formulation of claim 1, comprising pergolide mesylate, dimethyl sulfoxide, and benzyl alcohol, and further comprising polypropylene glycol.

11. The formulation of claim 4, comprising pergolide mesylate, and dimethyl sulfoxide, and further comprising polypropylene glycol.

12. The formulation of claim 1, wherein the solvent system is 46.7% dimethyl sulfoxide, 22.6% benzyl alcohol, and 30.7% polypropylene glycol.

* * * * *